Nov. 8, 1955 J. D. BROWNELL Plant Pat. 1,432
ROSE PLANT
Filed Dec. 7, 1954
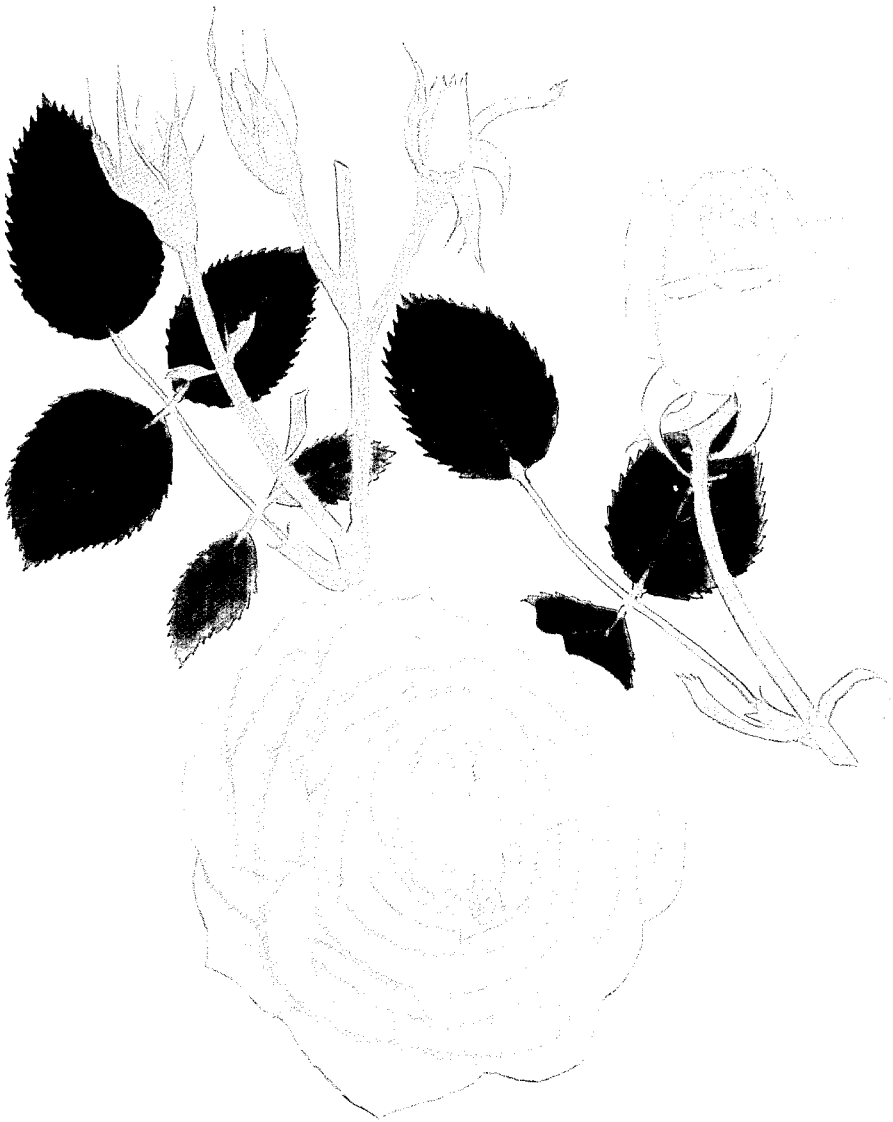
INVENTOR.
Josephine D. Brownell.

United States Patent Office

Plant Pat. 1,432
Patented Nov. 8, 1955

1,432

ROSE PLANT

Josephine D. Brownell, Little Compton, R. I.

Application December 7, 1954, Serial No. 473,771

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by selection of variety variations and by cross pollination, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States;

The deep red color (ordinary dictionary definition) of its petals, in combination with the unique brilliance thereof and their tendency to hold this color under exposure;

The novelty and variation within certain definite limits of the form of the bloom, its character of holding that form for a long time and the petallage of the flowers;

Its character of fragrance;

Its unusual abundance of flowers, notable after early bloom time and until frost;

The intensity of its remontant and everblooming or reblooming character and its large size;

Its character of ascending in height by recurrent branching and progressively longer stems from the base.

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot, under certain definite conditions of exposure, without any cultural control.

In the accompanying drawing forming a part of this specification I have shown my new rose in its natural colors, that is, as near as is possible to do so artificially.

My new rose is otherwise described as follows:

ESSENTIAL INFORMATION

*Type*

Hybrid tea, *Rosa wichuraiana* hybrid, dwarf ascending under normal conditions to about four feet tall, for garden display, cut flower and forcing or growing under glass.

*Class*

Hybrid tea crossed with *Rosa wichuraiana* hybrid, further restricted by originator to include only those varieties that can survive moderately low sub-zero temperatures.

*Breeding*

This variety was produced and bred by me and under my direction by propagation, selection and cross pollination.

It came into being as a seedling grown from a seed born on a seedling of which Mirandy, Plant Patent No. 632, was the pollen parent; the seed parent of my new rose was produced by crossing Pink Princess, Plant Patent No. 459, as pollen parent with Queen o' the Lakes, Plant Patent No. 1003, as seed parent.

The pollination that fertilized the seed that grew into my new rose, as well as the two previous pollinations that produced its two parents, were directed by me and were performed by emasculating flowers and placing thereon a bag protecting from self and foreign pollen. These bags were later removed and the flowers were hand pollinated with a camel's hair brush and the bags immediately replaced. The date of the pollination of my new rose was August 1, 1949.[1] The seed was planted for me and under my direction on December 20, 1949, and the date of the first flower was May 10, 1951.

The plant and flower seemed to me to be of unusual merit and I have since made and directed extensive propagations and tests thereof.

Plants of this variety budded from this seedling on to *Rosa multiflora* root stocks, have after being exposed to moderate sub-zero temperatures, survived and bloomed normally the following season in the hybrid tea manner. The variety has been propagated by budding at Little Compton, Rhode Island, on July 21, 1951, and thereafter and the characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three and occasionally more on each stem, in the usual hybrid tea type of cluster; of a more free flowering type than many commercial varieties of hybrid teas.

The pedicels and peduncles are medium in diameter and medium in length, erect, stiff, almost smooth, free from large prickles and bristles. Stems are long, diameter medium and moderately stiff and rigid.

*Quantity of bloom*

Free, being cumulative in quantity from year to year as the plant increases in size, flowering through the summer and fall.

*Fragrance*

Distinctive, pleasing china tea in combination with that of *Rosa wichuraiana*, under favorable environment.

*Bud*

Neck normal as described, opens well, being little to not at all affected by hot or wet weather or both, as to color and form, except at very high temperatures the color is less intense and the form of the petals is less recurled.

Before the calyx separates the size is medium, form moderately high pointed, the sepals are normal except occasionally with spurs irregularly spaced and distributed; and occasionally with small foliaceous tips, otherwise tapering to lanceolate at their apex, turning back nearly perpendicular to the pedicel as the bud opens.

Color of the bud as calyx opens, outside Currant Red at 821/3; color reference to English Horticultural Color Chart.[2]

*Bloom*

Outer petals gracefully recurled under normal environment. Color outside of petals, outer rows, Currant Red

[1] This and other dates herein are approximate.
[2] Color references to same unless otherwise indicated.

at 821/3 shading to Crimson at 22; inner petals, outer side, Crimson at 22. Inner side of petals, Currant Red at 821/2.

Color softens slowly to Crimson at 22/2 all sides of all petals.

Color slightly variable dependent upon quality of sun or other light.

The flower usually varies in size averaging around five inches in diameter when fully open, petals average between fifty and sixty, frequently some smaller petals and petaloids in the center, variable in form and number.

The flower opens moderately ovate and medium high centered, quite formal, with late display of stamens and pistils. The petals are variable from obovate to ovate to irregular and nearly formal as to arrangement and recurl, and edges of the smaller petals occasionally notably irregular. Texture is medium to thick; both sides brilliant. The time of opening in favorable conditions is about five days.

The petals are substantial and after about six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Productive organs*

Stamens, quantity variable, medium long of slightly uneven length.

Anthers, nearly Orpiment Orange at 10/1. Filaments, nearly Amber Yellow at 305/3.

Pistils are several of nearly even length, averaging about one-half inch long.

PLANT

*Foliage*

Is abundant, of compound leaves of three to five leaflets near the flower, five leaflets lower down the stem and frequently seven leaflets in the middle of the stems and nearer the base. Often with short narrow leafy formations variously positioned near the flower as shown. Size of leaflets medium. Form of leaflets usually nearly ovate with apex moderately acute, base rounded to slightly pointed in some instances; margins with slightly irregular medium pointed serrations, petiolules medium short, and with slightly wider space than usual between leaflets.

The leaflets average in width about one-half of their length.

Color of leaflets on the upper surface is slightly variable from Spinach Green at o960, irregularly shaded with Parsley Green at oo962, with reverse side nearly Asphodel Green, the last color reference is to Robert Ridgway Color Standards.

The rachises are moderately narrow to slender, upper side smooth except some very short hairs almost microscopic on edges. Under side moderately smooth, usually three to five short prickles.

Stipules are variable from normal medium short to irregular and long.

Plant habit, dwarf, becoming bushy to tall for a hybrid tea; from three to four feet in height, by stems from the base and by rebranching and growth and enlargement and extension of the stems. The growth is moderately free at first, developing more rapidly after one or two years under favorable vegetative opportunity.

Color of mature stems is Scheeles Green at 860/3, shading variously to nearly Parsley Green at oo962/2.

Prickles, several, frequently two to three between leaves, averaging in length about one-quarter to one-third inch, shading from Carmine at 21/2 to lighter at the base, turning lighter throughout and later to nearly colorless.

*Winter resistance*

A notable characteristic of this new rose is the resistance to moderate sub-zero temperatures in combination with its hybrid tea character, and its *Rosa wichuraiana* ancestry. The word temperature herein refers the Fahrenheit scale.

*Comparisons*

This rose variety is one of a new race or type of rose, not found in nature or in commerce, produced after more than forty years of intensive scientific research and combining by breeding several varieties containing different variations of expression, and using such resultant material as breeders.

The variety most nearly resembling my new rose is the *Rosa wichuraiana* hybrid Queen o' the Lakes Plant Patent No. 1003, which lacks some of the hybrid tea type of rebloom expressed by my new rose, notably that of the recurl which in my new rose is usually much more tightly and more formally recurled.

My new rose has more petals, is more upright in growth and the angle of growth of the stems is more nearly vertical.

My new rose has a different fragrance.

I claim:

A new and distinct variety of rose plant, substantially as shown and described, characterized by its color, fragrance, form and upright manner of growth.

No references cited.